US00PP16404P3

(12) United States Plant Patent
Lyrene

(10) Patent No.: US PP16,404 P3
(45) Date of Patent: Apr. 4, 2006

(54) BLUEBERRY PLANT CALLED 'SPRINGHIGH'

(50) Latin Name: *Vaccinium corymbosum*
Varietal Denomination: Springhigh

(75) Inventor: Paul M. Lyrene, Gainesville, FL (US)

(73) Assignee: Florida Foundation Seed Producers, Inc., Greenwood, FL (US)

( * ) Notice: Subject to any disclaimer, the term of this patent is extended or adjusted under 35 U.S.C. 154(b) by 193 days.

(21) Appl. No.: 10/872,300

(22) Filed: Jun. 21, 2004

(65) Prior Publication Data

US 2005/0283866 P1 Dec. 22, 2005

(51) Int. Cl.
*A01H 5/00* (2006.01)

(52) U.S. Cl. ..... Plt./157

(58) Field of Classification Search ..... Plt./157
See application file for complete search history.

*Primary Examiner*—Anne Marie Grunberg
*Assistant Examiner*—Annette H Para

(57) ABSTRACT

A new and distinct low-chill southern highbush (*Vaccinium corymbosum*) cultivar. Its novelty lies in the following unique combination of features:

1. Has a low chilling requirement.
2. Has a vigorous, upright bush.
3. Produces large berries with small, dry picking scar and good firmness, flavor and texture.
4. Ripens its crop early in the season, with most of the harvest in northest Florida coming between April 15 and May 10.

4 Drawing Sheets

Latin name of the genus and species: *Vaccinium corymbosum* L.
Variety denomination: 'Springhigh'.

BACKGROUND OF THE INVENTION

Southern highbush blueberries are a domesticated form of *Vaccinium corymbosum* which were bred by lowering the chilling requirement of northern highbush blueberries, which were first domesticated in New Jersey between 1910 and 1930. Northern highbush blueberry varieties require a minimum of 1000 hours below 7° C. per winter to stimulate opening of the flower and leaf buds in the spring. In the eastern United States, this limits their cultivation to areas that have winters at least as cold as those typical of the coastal plan of North Carolina around Wilmington. Due to low temperatures from February through April, blueberries in this area do not ripen before mid-May. In the southern hemisphere, northern highbush varieties do not ripen before mid-November. The principal utility of southern highbush blueberries is that their low chilling requirement, achieved through breeding, allows them to be grown in areas where warm temperatures in late winter and early spring permit flowering in early February and ripening in April and early May in the northern hemisphere and flowering in early August and ripening in October and early November in the southern hemisphere. Thus, southern highbush blueberries extend the season of availability of fresh blueberries by a period of about 6 weeks in each hemisphere and contribute to the year-round availability of blueberries on the fresh market. Because southern highbush blueberries are relatively new, additional varieties are needed that have higher yields, varying dates of maturity, and adaptation to various production areas.

'Springhigh' was developed by the University of Florida in its southern highbush blueberry-breeding program. The seedling that became 'Springhigh' came from the cross FL91-226 (unpatented)×'Southmoon' (U.S. Plant Pat. No. 9,834), which was made in a greenhouse in March 1993. The seedling was transplanted to a field nursery in May 1994. It fruited and was evaluated in the spring of 1995 and 1996 and was propagated by softwood cuttings in June 1996. A test plot of 24 rooted cuttings was planted on a commercial blueberry farm at Windsor, Fla. in January 1997. Three additional plots, each with 50 plants or more were planted at Windsor and a 200-plant plot was planted at Archer, Fla. The youngest of these plots had their second berry crop in the spring of 2003. The principal attractive features of the clone are its strong, upright bush and its early fruit ripening.

BRIEF SUMMARY OF THE INVENTION

'Springhigh' is a new southern highbush variety that has the following unique combination of characteristics that set it apart from other blueberry cultivars.

a. Ripens very early, with the first 50% of the berries ripe between April 18 and April 25 at Windsor, Fla. This average is 9 days earlier than the mean for 'Star' (U.S.Plant Pat. No. 10,675), 'Windsor' (12,783), 'Millennia' (12,816), 'Emerald' (12,165), and 'Jewel' (11,807).

b. Produces a strong, upright bush.

c. Has a chilling requirement of 200 to 300 hours below 7° C.

d. Berries large; first ripe berries average 3.0 g.

e. Berries have high firmness and a dry picking scar.

f. Springhigh differs from its parents in many details, as would be expected for a seedling from a cross between two highly heterozygous clones. Compared to parent FL91-226, 'Springhigh' has a more upright bush habit and produces a much larger berry with better berry firmness. Compared to parent 'Southmoon', 'Springhigh' ripens 3 weeks earlier, has much better resistance to phytophthora root rot, and produces a larger berry with a somewhat darker berry color.

BRIEF DESCRIPTION OF THE DRAWING

The color chart used in this specification is "The Pantone Book of Color", by Leatrice Eiseman and Lawrence Herbert. 1990. Harry N. Abrams, Inc., Publishers, N.Y. Where colors in the drawings differ from the Pantone color designations in the verbal descriptions, the Pantone color designations are the more accurate.

FIG. 2 shows a row of 4-year old plants in May after harvest. The plants are about 2 m tall. The upright growth habit and dark green leaves are characteristic.

DETAILED BOTANICAL DESCRIPTION

Figure 1:
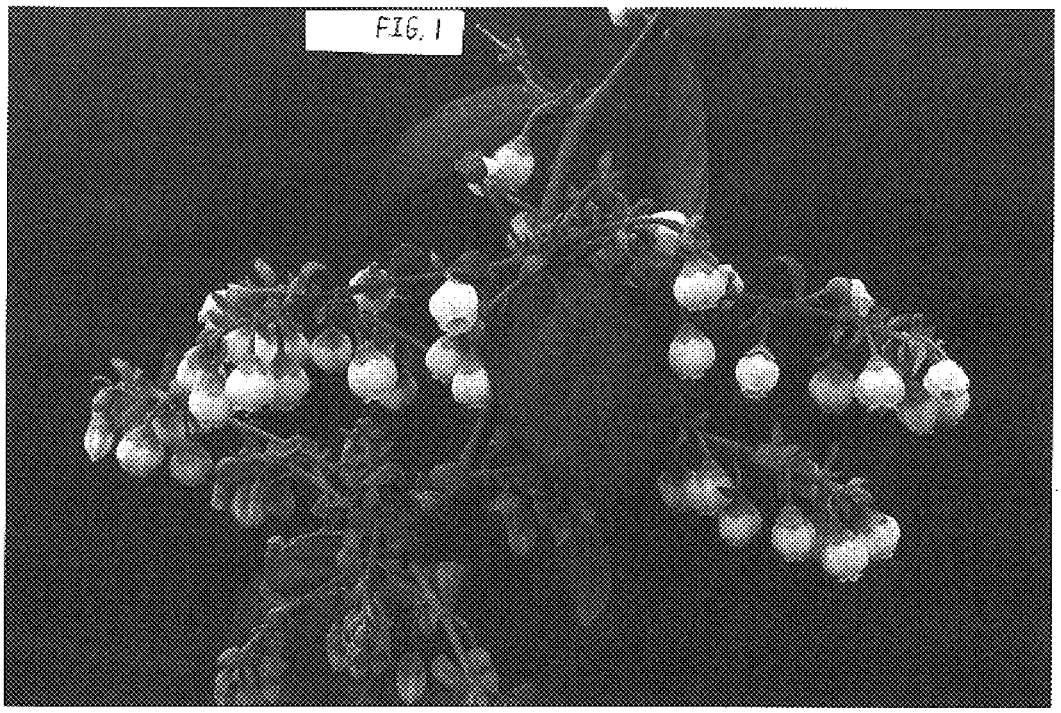
FIG. 1 shows flower clusters of 'Springhigh' during February on young plants that were maintained evergreen in a greenhouse. This environment elongates the peduncles compared to what would be seen on field-grown plants that have been chilled before flowering. The white corollas and urceolate flowers are typical.
Figure 3:
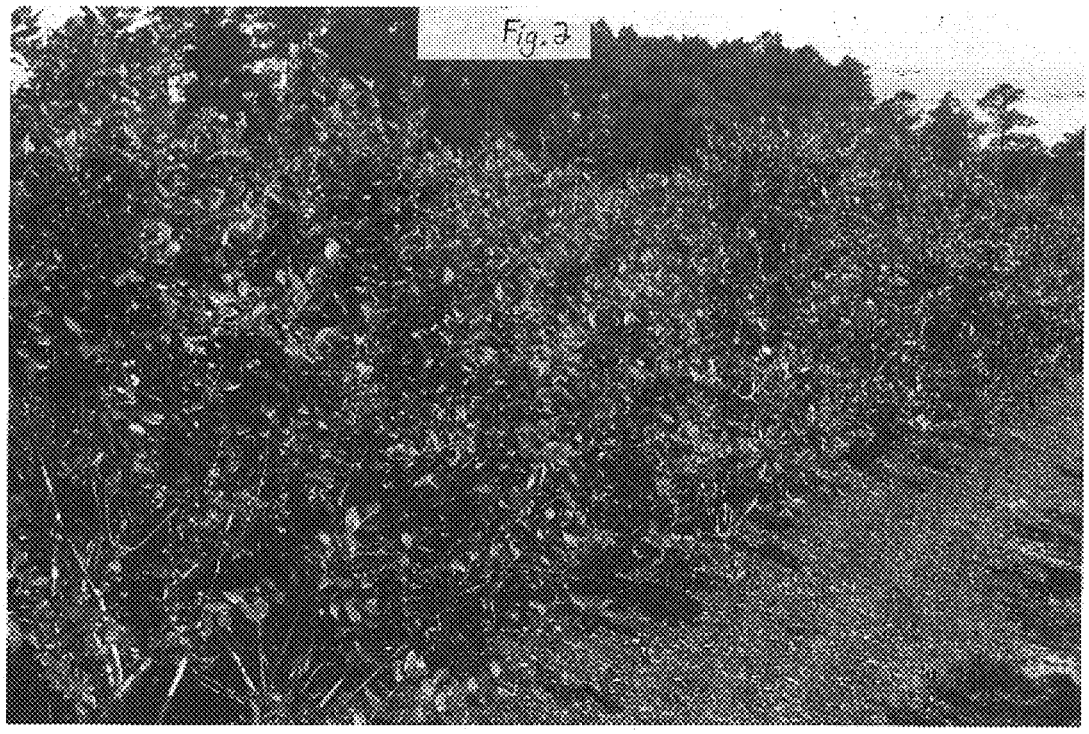
FIG. 3 shows at close range a cluster of berries in early May on a field-grown plant. The dark green leaves and rather dark berries are typical.
Figure 3:
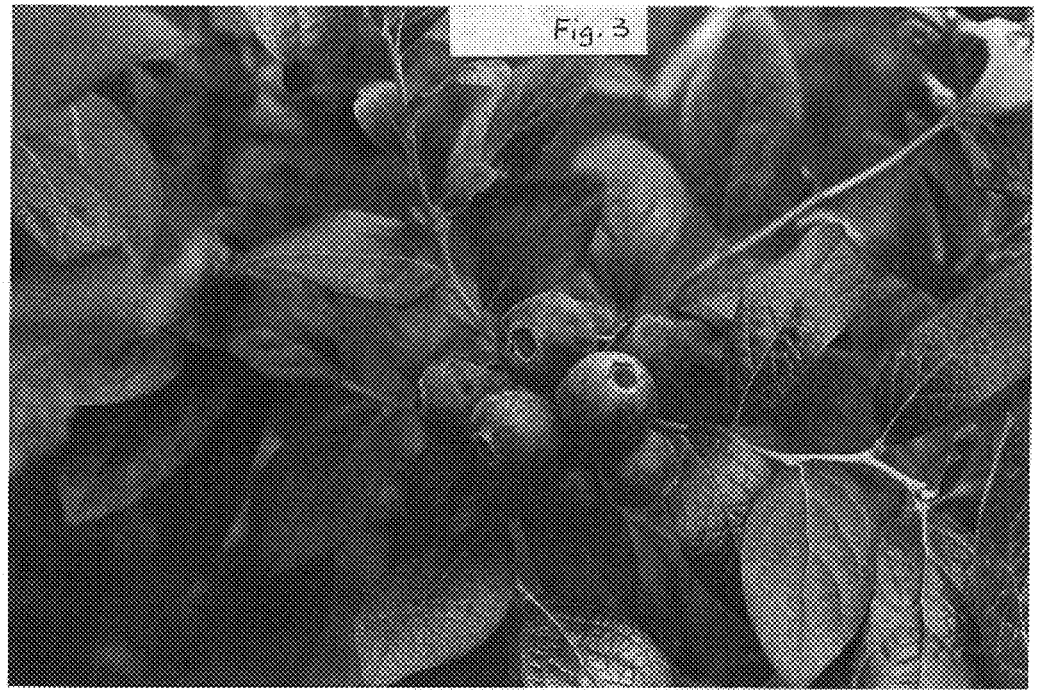
Figure 4:
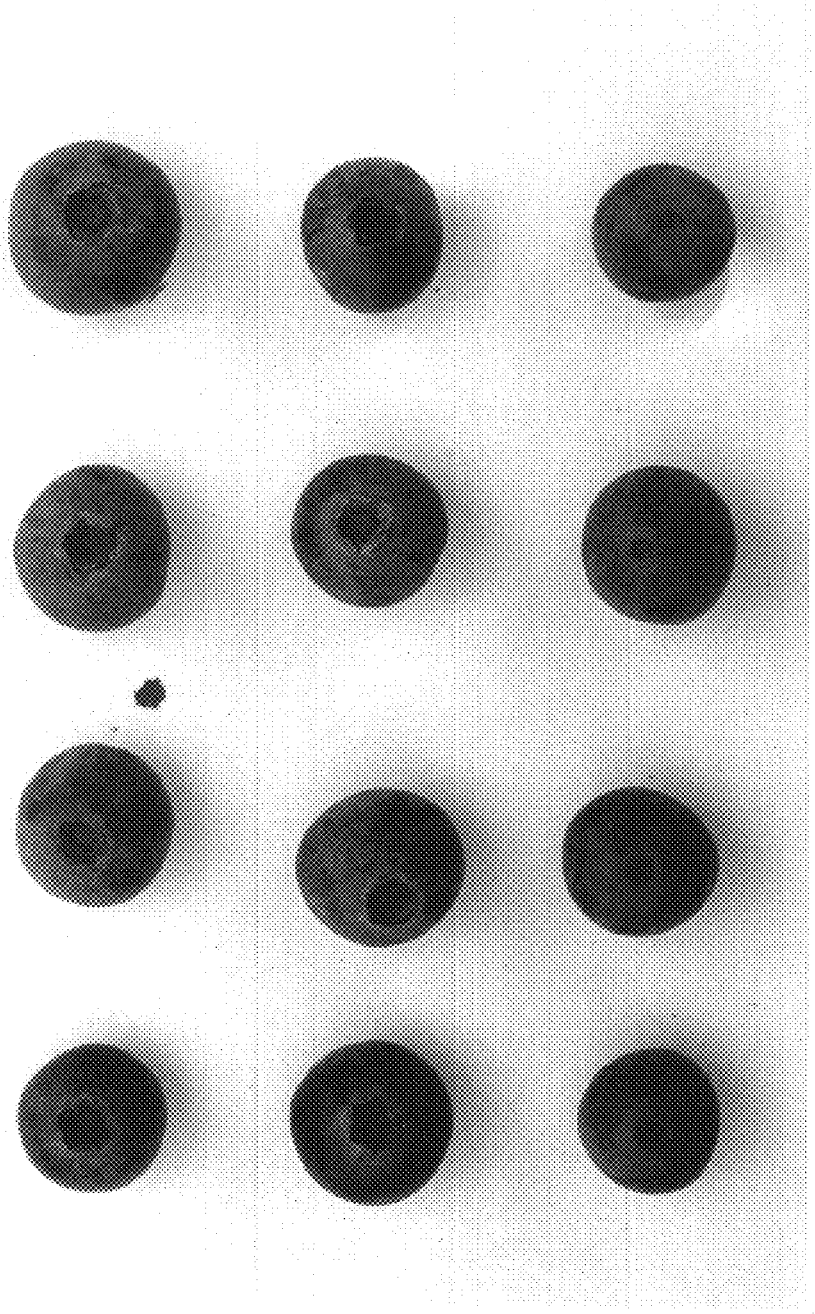
FIG. 4 shows, at close range, the mature berries. The rather undeveloped calyx lobes can be seen in the two columns at the left and the medium to small picking scar can be seen in the column at the right.

Market class: 'Springhigh' produces southern highbush blueberries suitable for both the fresh and processed fruit markets.

Bush: Plant characteristics were measured on 6-year-old plants in a commercial field at Windsor in north Florida. The field had been irrigated, pruned, and managed according to recommended procedures for commercial blueberry farms in north Florida.

*Plant height.*—2.2 m.

*Canopy diameter measured at widest part of the bush.*—1.5 m.

*Plant vigor.*—High. Equal to 'Millennia' (U.S. Plant Pat. No. 12,816) and 'Emerald' (U.S. Plant Pat. No. 12,165) and more vigorous than 'Star' (U.S. Plant Pat. No. 10,675).

*Growth habit.*—Upright, with multiple upright canes from the base.

*Flower bud density (number) along flowering twigs in January.*—High.

*Twigginess.*—Low.

Trunk and branches:

*Suckering tendency.*—Medium to low. Six to 10 major canes arising from a base 30 cm in diameter on 6-year-old plants.

*Surface texture of strong, 6-month-old shoots observed August 18.*—Smooth.

*Surface texture of strong, 1-year-old shoots observed August 18.*—Becoming rough as vertical cracks appear in the smooth stem and rough, corky bark fills the cracks.

*Surface texture of 3-year-old and older wood surface.*—Rough, but periodically exfoliating to for a relatively smooth exterior.

*Color of 6-month-old wood observed August 18.*—'Hay' (Pantone 12-0418).

*Color of 1-year-old rough bark observed August 18.*—'Sand' (Pantone 15-1225).

*Color of 3-year-old rough-textured canes.*—'Pebble' (Pantone 14-1112).

*Internode length on strong, upright shoots measured August 18.*—2.0 cm.

Leaves:

*Leaf length including petiole, from tip of petiole to end of blade.*—Mean 68 mm.

*Leaf width at widest point.*—Mean 36 cm.

*Leaf shape.*—Oval. Midrib terminates in a dew tip, which is about 0.4 mm long, visible under 15 X microscope.

*Leaf margin.*—Entire, but with a few sessile glands.

*Color of upper surface of leaves.*—'Avocado' (Pantone 18-0430).

*Color of lower surface of leaves.*—'Cedar' (Pantone 16-0526).

*Pubescence on upper surface of leaves.*—Variable from leaf to leaf but most leaves have short, white hairs on the midrib and major veins.

*Pubescence on lower surface of leaves.*—Most leaves are densely hirsute, with short, white, curved hairs along the midrib and major veins.

*Pubescence on leaf margins.*—None.

*Relative time of leafing and flowering.*—Under normal spring conditions, the plants flower and begin to produce new leaves at about the same time.

Flowers:

*Flowering arrangement.*—Flowers arranged alternately along a short, leafless, deciduous branch.

*Flower fragrance.*—None.

*Pedicel length at time of anthesis.*—3 mm.

*Peduncle length at time of anthesis.*—Variable; averages about 10 mm.

*Petals.*—Fused into a corolla tube with 5 lobes.

*Pollen staining.*—Approximately 99% of the pollen grains stain with acetocarmine dye, indicating that a high percentage of the pollen grains are well formed, starch filled, and potentially variable.

*Pollen abundance.*—Dried flowers shed pollen in abundance.

*Pollen color.*—'Golden rod', Pantone 14-0951.

*Flower type.*—Perfect, ovary inferior, petals fused into a corolla tube, the 10 stamens inserted at the base of the corolla tube.

*Flower length from pedicel attachment point to corolla tip.*—10 mm.

*Length of corolla tube.*—8 mm.

*Style length from top of ovary to stigma tip.*—8.5 mm.

*Calyx diameter at anthesis from tip of one lobe to tip of the opposite lobe.*—6 mm.

*Diameter of corolla tube at widest point.*—9 mm.

*Corolla aperture diameter.*—3.5 mm.

*Corolla surface texture.*—Smooth.

*Flower shape.*—Urceolate.

*Corolla color at anthesis.*—White— the color of the unprinted spaces in the Pantone Book of Color.

*Style color at anthesis.*—'Bright chartreuse', Pantone 14-0445.

*Pedicel and peduncle color.*—'Moss', Pantone 16-0532.

*Flowering period.*—Average date when the first 50% of the flowers open at Gainesville, Fla. is February 16. This compares with the following dates for some other varieties: Emerald (U.S. Plant Pat. No. 12,165): February 20; 'Jewel' (U.S. Plant Pat. No. 11,807): February 20; Millennia (U.S. Plant Pat. No. 12,816): February 19; Star (Plant Pat. No. 10,675): March 2.

*Flower cluster* (*tight, medium, or open*).—Medium.

*Average number of flowers per cluster.*—10.

*Location of tip of stigma relative to the lip of the corolla.*—The tip of the stigma extends equally far as the tips of the corolla lobes.

*Distance between the stigma tip and the part of the anther pore nearest the stigma tip.*—2.5 mm.

Berry:

*Mean date of first commercial harvest* (*25% of fruit ripe*) *at Windsor, Fla.*—April 16.

*Mean date of last commercial harvest.*—May 15.

*Diameter of calyx aperture on mature berry.*—Mean 6.4 mm.

*Calyx lobes on mature berry.*—Size and shape. Not well developed. Inconspicuous and pressed flat against the surface of the berry.

*Berry cluster:* (*tight, medium, or loose*).—Medium to loose.

*Pedicel length on ripe berry.*—4.6 mm.

*Peduncle length at the time berries are ripe.*—Mean 13 mm but quite variable form cluster to cluster.

*Number of ripe berries per cluster.*—Mean 4.

*Mean berry weight on well-pruned plants.*—3.0 g.

*Mean berry height.*—14.3 mm.

*Mean berry width.*—17.6 mm.

*Surface color of ripe berry while on plant.*—'Pewter' (Pantone 18-5203).

*Surface color of ripe berry after harvest and packing.*—'Shale' (Pantone 19-3903).

*Surface color or ripe berry after polishing.*—Shiny black.

*Internal flesh color of ripe berry.*—'Overcast' (Pantone 14-0105).

*Berry surface wax.*—Sparse to medium in abundance and easily removed by handling.

*Berry pedicel scar.*—Small and dry.

*Berry firmness.*—High.

*Berry flavor.*—Sweet, low acid.

*Berry texture.*—Good: small seeds, very juicy, thin skin.

*Color of dried seeds.*—'Hazel' (Pantone 17-1143).

*Weight of well-developed dried seeds.*—0.46 mg.

*Length of well-developed, dried seeds.*—1.7 mm.

*Width of well developed, dried seeds.*—1.0 mm.

Physiological characteristics:

*Chilling requirement.*—200 to 300 hours below 7° C.

*Cold hardiness.*—Flowers and fruit hardy to −3° C. The plant, during winter dormancy is hardy to −15° C.

*Productivity.*—In northeast Florida, 'Springhigh' produces about 5 pounds of berries per bush on plants 4 years old and older.

*Ease of propagation.*—'Springhigh' is easy to propagate from softwood cuttings. Several hundred plants have been propagated by this method in Gainesville, Fla., and all are typical of the variety.

Resistance to diseases, insects, mites:

*Phytophthora root rot.*—High.

*Stem blight* (*Botryosphaeria dothidea*).—High.

*Cane canker* (*Botryosphaeria corticis*).—High.

*Fungal leaf spots.*—Above average resistance for southern highbush blueberry. Fungicidal control of leaf diseases will probably be needed in commercial plantations in areas with humid summers where the pathogens are present.

*Overall survival in the field.*—Good. The plant appears to survive better in the field than most other southern highbush varieties grown in Florida.

It is claimed:

1. A new and distinct southern highbush blueberry plant, substantially as illustrated and described, characterized by having a vigorous, upright, durable bush that produces large berries that ripen very early in the season.

* * * * *